(12) United States Patent
Phillips

(10) Patent No.: US 7,621,882 B2
(45) Date of Patent: Nov. 24, 2009

(54) MEDICAL DEVICE FOR A USER'S LIMB

(76) Inventor: Anthony G. Phillips, P.O. Box 723, Suffield, CT (US) 06078

(*) Notice: Subject to any disclaimer, the term of this patent is extended or adjusted under 35 U.S.C. 154(b) by 53 days.

(21) Appl. No.: 11/890,015

(22) Filed: Aug. 3, 2007

(65) Prior Publication Data
US 2008/0039755 A1    Feb. 14, 2008

Related U.S. Application Data

(60) Provisional application No. 60/835,921, filed on Aug. 7, 2006.

(51) Int. Cl.
*A61F 5/00* (2006.01)

(52) U.S. Cl. .................. 602/20; 602/21; 602/23

(58) Field of Classification Search ............... 602/5, 602/23, 26, 27; 2/16, 22, 24, 44, 46, 59, 2/62; 128/878, 879, 882
See application file for complete search history.

(56) References Cited

U.S. PATENT DOCUMENTS

| | | | | |
|---|---|---|---|---|
| 5,074,853 | A * | 12/1991 | Bryant | 604/349 |
| 5,925,010 | A * | 7/1999 | Caprio, Jr. | 602/62 |
| 6,483,087 | B2 * | 11/2002 | Gardner et al. | 219/545 |
| 6,490,736 | B2 * | 12/2002 | Phillips | 2/242 |
| 2002/0073480 | A1 * | 6/2002 | Phillips | 2/455 |

* cited by examiner

*Primary Examiner*—Michael A. Brown

(57) ABSTRACT

A medical device removably secured to a limb of a user. The medical device includes at least one liner, at least one pocket, at least one protective panel, and/or blotter means for indication discharge of fluid.

12 Claims, 3 Drawing Sheets

Fig. 1
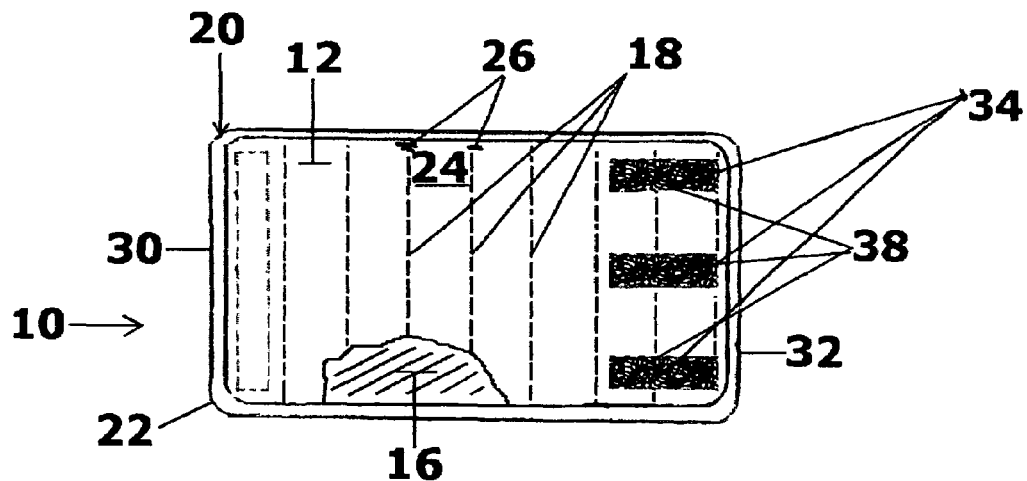
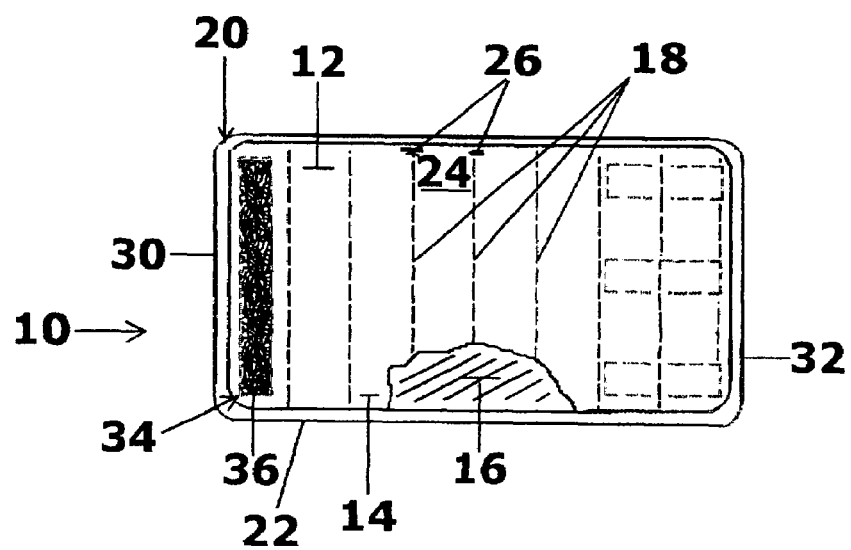
Fig. 2

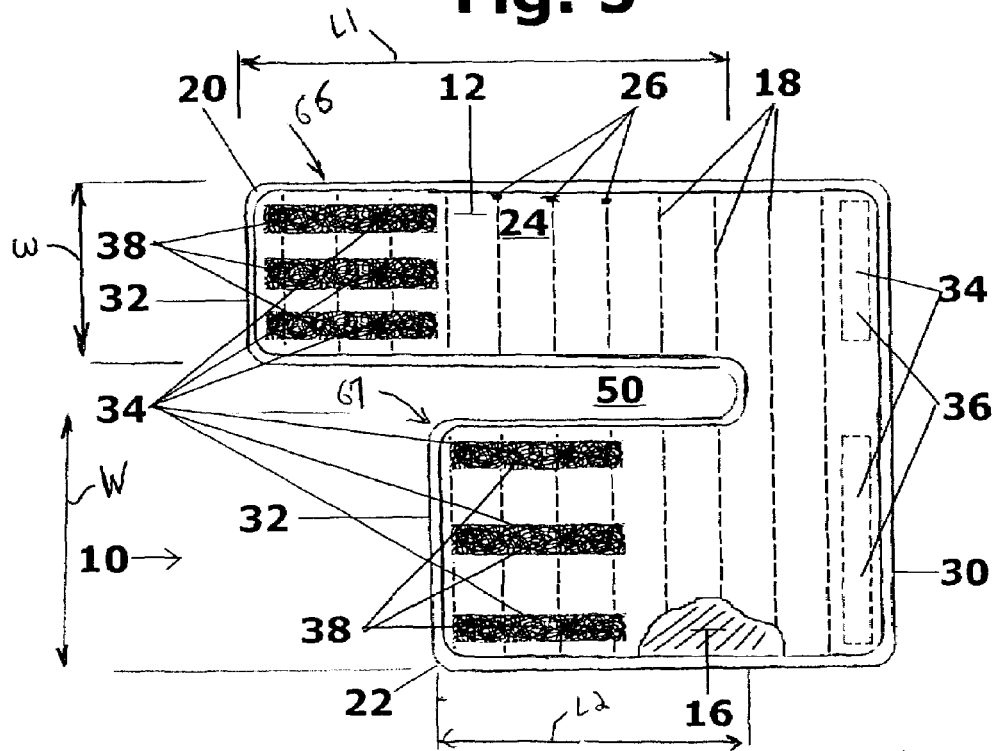
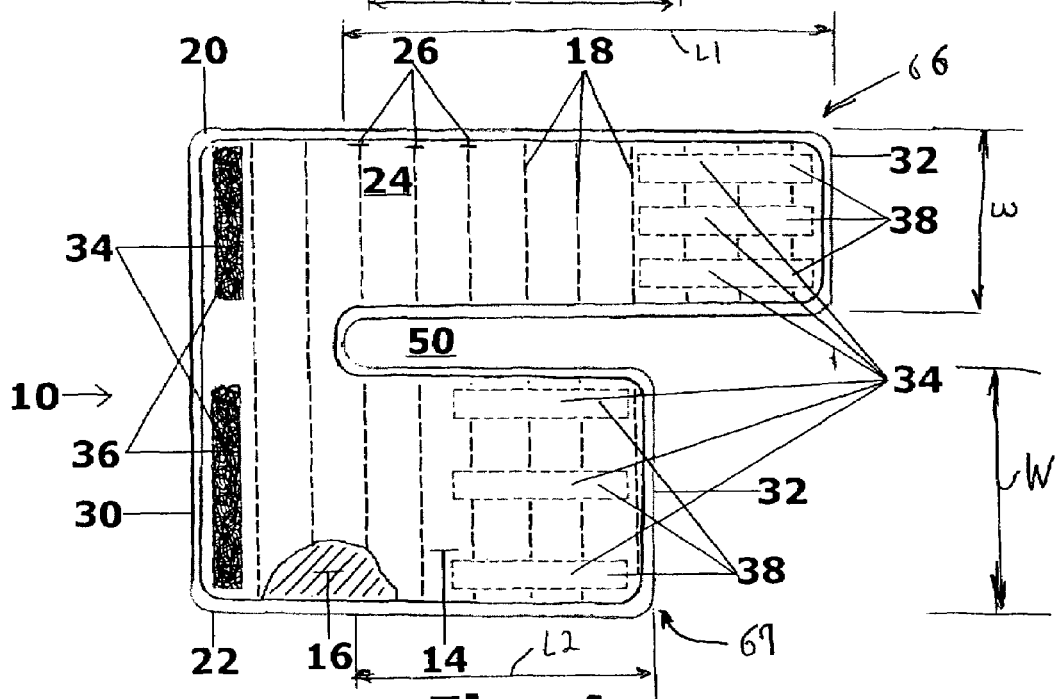

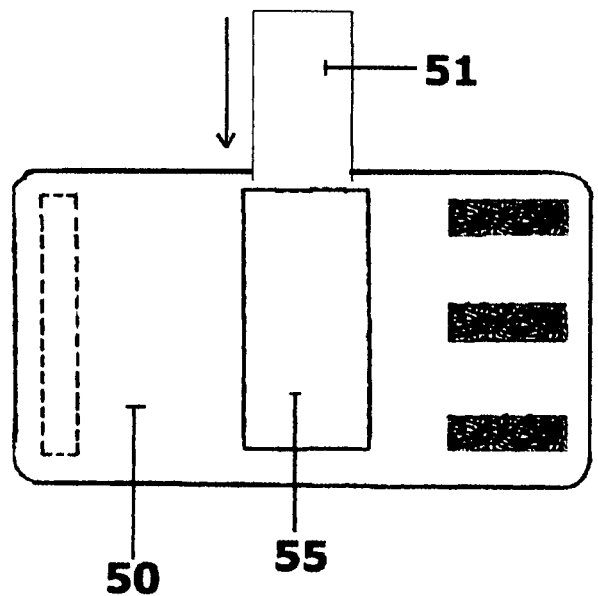
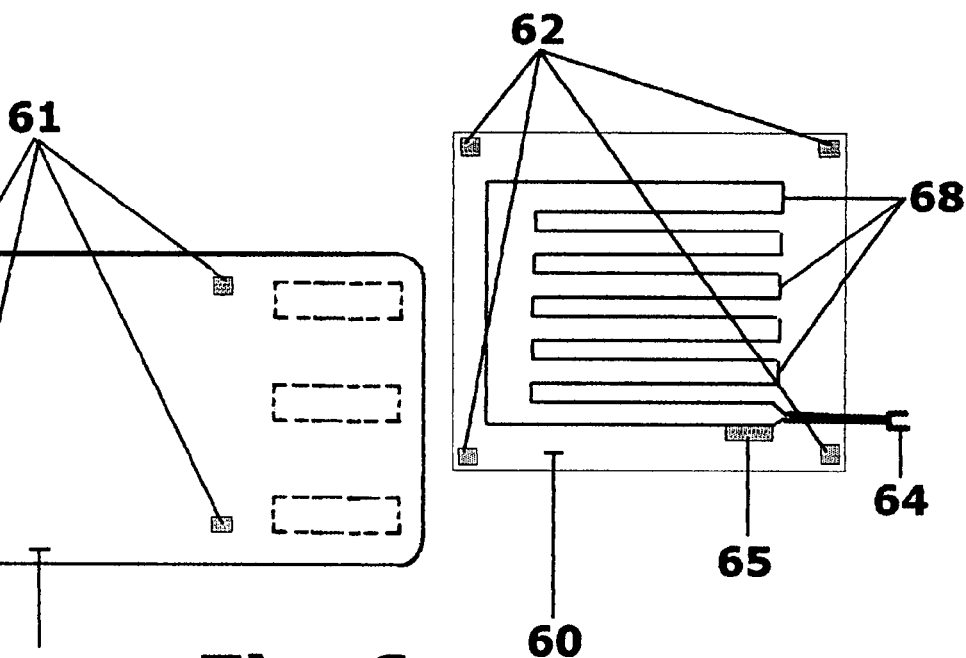

MEDICAL DEVICE FOR A USER'S LIMB

CROSS REFERENCE TO RELATED APPLICATION

This application claims priority to U.S. provisional patent application Ser. No. 60/835,921, filed Aug. 7, 2006, which is herein incorporated by reference in its entirety. This application is related to U.S. Pat. No. 6,463,594, issued Oct. 15, 2002; U.S. Pat. No. 6,490,736, issued Dec. 10, 2002; and U.S. Pat. No. 6,553,578, issued Apr. 29, 2003, the subject matter of which are incorporated herein by reference in their entirety.

FIELD OF THE INVENTION

This present invention relates generally to a medical device, in particular to a medical device for removably securing to a limb of a user.

BACKGROUND OF THE INVENTION

In the healthcare, industry medical devices are used to attached to a users limb to treat various medical conditions. However, the limb of a user can vary in size and shape depending on the condition of the limb, the amounting of swelling in the limb, whether an amputation of at least a portion of the limb is involved, the condition of the user's skin and/or the presence of other medical devices such as bandages. Therefore, there is a need for an inventive medical device which is adjustable to the size, shape, configuration and condition of the user's limb. There is also a need for a medical device which provides compression of the user's limb, which adds or removes heat from the limb, protects the user's limb and indicates the condition of a user's limb.

Prior medical devices, such as a protective surgical dressing in the form of a bandage (e.g., Band-Aid® Registration No. 0194123) which often utilize adhesives to affix the bandage to a wearer. This is disadvantageous since it greatly reduces the useful life of the medical device to as few as one use. Thus three is a need to maximize the useful life of the medical device by utilizing methods of affixation such as, but not limited to, hook and loop fasteners.

There is also a need to improve the ease of which such medical devices can be secured to a user and minimize the dexterity needed to apply the medical device to the wearer by the wearer, or the caregiver of the wearer, who may be elderly, handicapped, challenged, or otherwise reduced in the capacity of dexterity.

SUMMARY OF THE INVENTION

In one aspect, the present invention is directed to a medical device including at least one layer of planar sheet of material defining opposed edge portions which is sized to extend around and partway along the limb of the wearer, wherein the medical device comprises one or more slots which extends from one of the opposed edge portions into the medical device. One of the opposed edge portion extends in a straight line, while the other opposed edge portion includes a first longitudinal member having a first length and a first width and a second longitudinal member having a second length and a second width. The first length and the second length are substantially equal lengths or different lengths and the first width and the second width are substantially equal widths or different widths. The first longitudinal member and second longitudinal member each include fastening means for joining said opposed edge portions, after the medical device is wrapped around the limb.

In another aspect of the present invention, a medical device is provided including at least one layer of planar sheet of material defining opposed edge portions which is sized to extend around and partway along the limb of the wearer; wherein the medical device defines one or more slots that are approximately U-shaped which extends from one or more of said opposed edge portions into said medical device; and fastening means for joining the opposed edge portions, after the medical device is wrapped around the limb.

In another aspect of the present invention, is directed to a medical device worn about an appendage of a wearer comprising: rectangular facing and backing planar layers being coupled to one another and sized to extend around and partway along the appendage, with the coupled layers defining opposed free edges; a layer of insulating material is interposed between the planar layers that include a quilted pattern of closely spaced lines of stitching; a reinforced stitching is sewn over at least part of one of the lines of stitching; a stitched binding is sewn along an outer periphery of the medical device; and fastening means for releasably joining the opposed free edges, after the medical device is wrapped around the appendage; wherein first and second hook and loop fasteners include at least one first and second strip of material having hook and loop material thereon, that are substantially perpendicular to one another, with the first strip secured to one of the opposed edge at an inner surface while the second strip is adjacent to the other of the opposed free edges at an outer surface.

In another aspect of the present invention, is directed to a tensioning means disposed between opposing ends of the device and to apply compression to a limb of a user, a comprising a protective panel disposed on at portion of the at least one layer of planar sheet of material, an insulating material to retain heat in a limb of a user for effecting circulation of blood within the limb of the user, at least one of a heat input device and a heat removal device for controlling temperature of a limb of a user, at least one pocket disposed on one at least one of said layers of planar sheet of material, a blotter for indicating discharge of fluid for the limb of a user, at least one removable liner, wherein the liner comprises at least one electric resistance heater, wherein the liner comprises applicator means for storing and delivering a topical solution to a limb of the user, and/or wherein the liner is comprised of at least one planar sheet of a material comprising tension means to compress a limb of a user.

BRIEF DESCRIPTION OF THE DRAWINGS

FIG. 1 is a front view of the first embodiment of the present invention.

FIG. 2 is a rear view of the first embodiment of the present invention.

FIG. 3 is a front elevational view of the left side of a pair of the second embodiment of the present invention partially cut away to show a layer of insulating material.

FIG. 4 is a rear elevational view of the left side of a pair of the first embodiment of the present invention partially cut away to show a layer of insulating material.

FIG. 5 is a front view of the first embodiment of the present invention comprising at least one pocket.

FIG. 6 is a front view of the first embodiment of the present invention comprising at least one liner and the liner comprising one embodiment which includes, but is not limited to, electrical components to produce warmth.

DETAILED DESCRIPTION OF THE PREFERRED EMBODIMENT

As shown in FIGS. 1, 2, 3, and 4, a medical device generally designated by the reference number 10 is shown having opposing edges 30, 32.

The MEDICAL DEVICE wraps around a limb and affixes thereto for treatment or an adjunct to treatment for a symptom, condition, complication, or the result of an injury, poor circulation, increased glucose, decreased oxygen, decreased skin temperature, or conditions or diseases such as but not limited to diabetes, diabetic neuropathy, night cramps, cramps, arthritis, restless leg syndrome, Raynaud's Syndrome, venous ulcers, ulcers, or chronic wounds of the wearer. The medical device treats or affects the circulation or circulatory system of the wearer and affects the oxygen transport in and around the user's limb.

The medical device combines one or more characteristic or component such as being comprised of at least one sheet of planar material, having at least one pocket, having at least one liner, and affixing quickly and easily with fasteners such as, but not limited to, hook and loop fasteners. The medical device is flexible in that it may extend over all or part of a limb which may also include the jointed part of the limb. The medical device may benefit the wearer by warming or cooling, protecting from injury or protecting from further injury, applying solutions, increasing circulation, altering physiology, helping wounds to heal faster, provide compression, In one embodiment shown in FIG. 1 and FIG. 2, hook and loop fasteners are used to fasten the opposed edges 30 and 32 of the MEDICAL DEVICE. Thus the opposed edges are removably fastened to one another and the medical device is removably secured to a limb of a user without the use of adhesives. At least one strip of hook, number 36 in FIG. 2, and at least one strip of loop, number 34 and 38 in FIG. 1, is required; three are shown.

To manufacture one MEDICAL DEVICE, at least one layer of planar sheet of material is cut into approximately a rectangle shape. The rectangle may be longer than it is high. In one embodiment, at least one of the planar sheets is an elastic material for maintaining tension between the opposing edges 30 and 32 and providing compression to a user's limb. While, at least one of the planar sheets is described as being an elastic material the present invention is not limited in this regard as a portion of at least one planar sheet is also contemplated without departing from the scope of the present invention.

One strip of hook fastener is affixed flat such as but not limited to being sewn along an edge of the MEDICAL DEVICE so that the hook fasteners are exposed such as reference number 36 in FIG. 2.

On the opposed or opposite side of the MEDICAL DEVICE as in FIG. 1, three strips of loop fastener are affixed flat such as but not limited to being sewn near the edge of the material, which is opposite to the edge to which the hook fastener was previously affixed as 32, 34, 38 of FIG. 1.

1) Each strip of loop fastener is affixed so that the loop fasteners are exposed.
2) Each strip of loop fastener is affixed approximately, but not limited to, parallel to the other strips of loop fasteners.
3) Each strip of loop fastener is affixed so that one of the sides of the strip is approximately three quarters of an inch, but not limited to, from the edge of the material opposite to the edge of the material to which the hook fastener was previously affixed.
4) One strip of loop fastener, 38, is affixed equidistant from the top edge and the bottom edge of the material.
5) One strip of loop fastener, 34, is affixed so that one of its sides is approximately three quarters of an inch from the top edge of the material.
6) One strip of loop fastener, 32, is affixed so that one of its sides is approximately three quarters of an inch from the bottom edge of the material.

It is understood that the medical device described in FIG. 1 and FIG. 2 is by example only and does not limit the invention. This invention contemplates variations in the type of fasteners, number of fasteners, position of the fasteners, methods of affixing the fasteners, shape of fasteners, type of material, number of sheets of material, composition of material, shape of the invention, and size of the invention and is not limited in these regards.

The medical device described in FIG. 1 and FIG. 2 may also be comprised of more than one planar sheets of material affixed on all edges and comprising a pocket of gases, or compressed gases, such as, but not limited to air or oxygen. This pocket of gases when wrapped around a limb will provide compression to the part of the body of the wearer surrounded by the medical device.

The medical device described in FIG. 1 and FIG. 2 may also be comprised of, but not limited to, valves and plastic tubes which may be filled with gases, or compressed gases such as, but not limited to, oxygen. Said tubes may be, but are limited to, a similar pattern affixed to the medical device similar to liner 60 in FIG. 5. The medical device described in FIG. 1 and FIG. 2 may also comprise a container of compressed gases, such as, but not limited to, oxygen which may be released into the tubes and creating compression on the part of the wearer limb surrounded by the medical device. Said tubes may also be supplied gases, or compressed gases, from sources outside of the medical device described in FIG. 1 and FIG. 2. Said tubes may also be deflated by releasing gases through one or more valves.

As shown in FIGS. 3 and 4, a medical device generally designated by the reference number 10 includes a facing layer of material 12 and a backing layer of material 14. The facing and backing layers of material 12 and 14, respectively, are approximately the same size and shape and include a layer of insulating material 16 interposed between them.

In the illustrated embodiment, the facing, backing and insulating layers 12, 14, and 16, respectively, are sewn together and include lines of stitch 18 which cause the medical device 10 to become quilted. Preferably, the lines of stitch 18 are formed using quilting thread; however, the invention is not limited in this regard as other types of material known to those skilled in the pertinent art to which the invention pertains can be substituted for the quilting thread without departing from the broader aspects of the present invention.

In the illustrated embodiment, the medical device 10 defines an outer periphery 20 covered by a bias 22. In addition, the lines of stitching 18 forming the quilting include portions 24 having a pattern of closely spaced reinforcing stitches 26 adapted to prevent the quilting from coming apart during wear.

The medical device 10 defines opposing sides 30 and 32, adjacent to which are attached fasteners 34 for joining these ends together when the medical device is wrapped around the limb of a user. In the illustrated embodiment, these fasteners 34 are in the form of hook and loop fastening material with a plurality of strips (two shown) of hooked material 36 extending along one of the said opposed edges 30, and a plurality of strips (six shown) 38 of looped fastening material being attached adjacent to the other of the opposing ends 32 approximately perpendicular to the strips of hooked material. However, the present invention is not limited in this regard as the hooked and looped strips of material 36, 38 can be substituted for one another without departing from the broader aspects of the present invention. Moreover, while hook and loop fasteners are shown and described, the present invention is not limited in this regard as other types of fasteners, such as, but not limited to, buttons or zippers can be employed without departing from the broader aspects of the present invention.

The medical device 10 defines a slot 50 that extends inwardly from one of the opposed edges of the medical device. In the illustrated embodiment, the slot is shown as being approximately U-shaped; however, the invention is not limited in this regard as other shaped slots such as rectangular, triangular, or hourglass may be substituted without departing from the broader aspects of the present invention. The slot 50 is designed to be positioned over a joint such as the elbow or knee of the wearer, thereby preventing bunching of the medical device behind the joint causing discomfort to the wearer; however, the invention is not limited in this regard as material may be sewn or affixed over the slot 50 without departing from the broader aspects of the present invention. A medical device of FIGS. 3 and 4 illustrate at least one layer of planar sheet of material defining opposed edge portions which is sized to extend around and partway along the limb of the wearer; wherein the medical device comprises one or more slots 50 which extends from one of the opposed edge portions into the medical device. One of the opposed edge portions extends in a straight line. In one embodiment the other opposed edge portion includes a first longitudinal member 66 extending further than a second longitudinal member 67. The first longitudinal member 66 and second longitudinal member 67 include fastening means 38 for joining the opposed edge portions 30, 32, the medical device is wrapped around the limb. In one embodiment the second longitudinal member 66 has a width W and a length L1 and the first longitudinal member 67 has a width w and a length L2. In one embodiment the width W is greater than the width w, for adapting to different portions of a users limb and/or amputated and/or disfigured portions of a users limb. In one embodiment the width w is greater than the width W, for adapting to different portions of a users limb and/or amputated and/or disfigured portions of a users limb. In one embodiment the width W is substantially equal to the width w, for adapting to different portions of a users limb and/or amputated and/or disfigured portions of a users limb. In one embodiment the length L1 is greater than the length L2, for adapting to different portions of a users limb and/or amputated and/or disfigured portions of a users limb. In one embodiment the length L2 is greater than the length L1, for adapting to different portions of a users limb and/or amputated and/or disfigured portions of a users limb. In one embodiment the length L1 is substantially equal to the length L2, for adapting to different portions of a users limb and/or amputated and/or disfigured portions of a users limb.

While the present invention has been shown and described as being fabricated from layers of nylon and insulating material, the invention is not limited in this regard as other textile or non-textile material, such as leather, which would not require layering or reinforcing stitches, could be substituted without departing from the broader aspects of the present invention.

Preferably, the layer of insulating material 16 is made from a 10.5 ounce polyester batting material with the facing layer of material 12 being 200 denier nylon coated with polyurethane and the backing layer material 14 being 68 denier nylon. However, the invention is not limited in this regard as other weights of water-resistant, water-proof, or water-repellant coatings other than polyurethane, can be substituted, as can other suitable materials for facing and/or backing, without departing from the broader aspects of the present invention. In addition, the medical device 10 shown in FIGS. 3 and 4 as being sized to extend approximately the full length of the user's limb. However, the medical device can be sized to extend partway up a limb, or example, slightly above or below the knee or elbow of the user. During use of the medical device 10, a wearer would wrap the medical device around his or her limb, attaching the opposing edges with the hook and loop fasteners. The plurality of strips extending along one of the opposed edges 30, 32 allow for adjustment of the medical device to accommodate larger or smaller limbs.

The present invention contemplates various material, fasteners, affixing fasteners, affixing liners, affixing pockets, affixing components, composition of material, absorbency of material, shape of invention, size of invention, shape of liners, size of liners, positioning of fasteners, positioning of liners, number of liners, number of pockets, positioning of pockets, methods of affixing, It is understood that the medical device described in FIGS. 1, 2, 3, 4, 5 and 6 is by example only and does not limit the invention. This invention contemplates variations in the type of fasteners, number of fasteners, position of the fasteners, methods of affixing the fasteners, shape of fasteners, type of material, number of sheets of material, composition of material, shape of the invention, and size of the invention and is not limited in these regards.

In one embodiment of the medical device 50 shown in FIG. 5 includes a pocket 55 affixed to the facing layer 14 on three sides by sewing. The pocket 55 is open one side for removably receiving a device 51. In one embodiment the device 51 is a refrigerated chemical pack. In one embodiment the device 51 is a heated chemical pack. In one embodiment the device 51 is a protective panel configured to fit over a portion of a user's limb, a partial limb of a user (e.g., partial amputated limb) or over a disfigured limb of the user for protecting the user's limb from trauma or impact. In one embodiment the protective panel is configurable or moldable in-situ on the user's limb. In one embodiment, the panel sets to form an impact resistant surface after in-situ molding or configuring. The protective panel is manufactured from plastic, metal, wood, or leather. While the pocket 55 is described as being affixed to the facing layer 14 the present invention is not limited in this regard as the present invention is also adaptable to having the pocket affixed to the backing layer 12. Although FIG. 5 illustrates one pocket, the present invention is not limited in this regard as one or more pockets are also contemplated within the scope of the present invention.

The embodiment of the medical device 63 shown in FIG. 6 comprises one or more liners 60 affixed by, but not limited to, hook and loop fasteners, shown as 61 and 62 interchangeably to the back of the invention. Liner 60 is comprised of, but not limited to, electrical resistance heater 68, an electrical plug 64, and an electrical temperature control device 65 which is intended to input heat to the limb of a user thereby warming the user's limb. The liner 60 is comprised of at least one planar sheet of material for applying medical solutions such as topical solutions and/or anti-microbial solutions thereto. In one embodiment, the liner includes a surface for dispensing the medical solutions therefrom onto the user's limb.

Liner 60 may also be comprised of, but limited to, a heat exchanger including tubing which may be, but is not limited to, plastic which is intended to circulate fluid such as, but not limited to, water which may be warmed or cooled.

Liner 60 may also be comprised of, but is not limited to, at least one sheet of planar material which is absorbent to allow the material to be treated with at least one, but not limited to, solution or medication with the intent of storing and subsequently applying the solution or medication to the wearer.

Liner 60 may also be comprised of, but not limited to, valves and plastic tubes which may be filled with gases, or compressed gases such as, but not limited to, oxygen. Said tubes may be, but are limited to, a similar pattern affixed to the Liner 60. Liner 60 may also comprise a container of compressed gases, such as, but not limited to, oxygen which may be released into the tubes and creating compression on the part of the wearer limb surrounded by the medical device. Said tubes may also be supplied gases, or compressed gases, from sources outside of liner 60.

The tubes may also release gases through valves.

Liner 60 may also be comprised of more than one planar sheets of material affixed on all edges and comprising a pocket of gases, or compressed gases, such as, but not limited to air or oxygen. This pocket of gases when wrapped around a limb will provide compression to the part of the body of the wearer surrounded by liner 60. Liner 60 may also comprise valves and means, such as, but not limited to, containers of gases, or compressed gases, such as, but limited to, air or oxygen with which to inflate or deflate the pocket of liner 60.

In one embodiment the planar sheet includes a blotter portion which is lightly colored, for example, white, for indicating discharge of fluid for the limb of a user and/or to identify or notice an injury is inside the medical device. Fluids, such as blood, pus, or a discharge from an injury may be more noticeable on the white material than other colors of material such as black. In one embodiment, the liner includes the blotter portion which is lightly colored, for example white.

While preferred embodiments have been shown and described, various Modifications and substitutions may be made without departing from the spirit and scope of the invention. Accordingly, it is to be understood that the present invention has been described by way of example, and not by limitation.

What is claimed is:

1. A method of using a medical device, the method comprising the steps of extending at least one planar sheet of material having opposed edge portions, around the limb of a wearer, said planar sheet of material comprising one or more slots which extends from one of the opposed edge portions of the planar sheet of material, one of said opposing edge portion extends outwardly, while the other said opposing edge portion includes a first longitudinal member comprising a first length and a first width and a second longitudinal member comprising a second length and a second width, a removable liner used to protect the limb of the wearer, said liner comprising an electric resistance heater, said heater comprising tubing located in the liner, placing said heater against the user's skin to apply heat to the user's limb, a blotter, using said blotter to detect any discharge of fluid from the user, a protective panel, said protective panel disposed on a portion of said planar sheet of material and fastening means, said fastening means used to hold the device around the user's limb.

2. The method of claim 1, comprising a tensioning means, said tensioning means is disposed between opposing ends of the device, applying compression to the user limb by pulling on the tensioning mean.

3. The method of claim 2, comprising the step of using an insulating material to retain heat in the limb of the user to effect circulation of blood within the limb of the user.

4. The method of claim 2, comprising the step of using a heat removal device to control the temperature of the user's limb.

5. The method of claims 4, wherein said liner comprises an applicator means, using said applicator means to store and deliver a topical solution to a limb of the user.

6. A medical device comprising a planar sheet of material having opposed edge portions, said sheet comprising one or more slots which extend from one of the opposed edge portions of the planar sheet of material, one of said opposing edge portions extends outwardly, while the other of said opposing edge portions comprises a first longitudinal member comprising a first length and a first width and a second longitudinal member comprising a second length and a second width, a removable liner adapted to encircle the limb of the wearer, said liner comprising an electric resistance heater, said heater comprising tubing located in the liner, a blotter adapted to detect any discharge of fluid from the user, a protective panel disposed on said planar sheet of material and fastening means used to hold the device around the wear's limb.

7. The medical device of claim 6, comprising a tension means disposed between opposing ends of the device to apply a compression to the wear's limb.

8. The medical device of claim 7, comprising an insulating material adapted to retain heat in a limb of a user for affecting circulation of blood within the limb of the user.

9. The medical device of claim 8, comprising at least one pocket disposed on said layer planar sheet of material.

10. The medical device of claim 9 comprising an applicator means for storing and delivering a topical solution to a limb of the user.

11. The medical device of claim 10, comprising a reinforced stitching sewn to said planar sheet of material, said stitching including a stitched binding sewn along an out periphery of said planar sheet of material.

12. The medical device of claim 11 comprising first and second hook and loop fasteners.

* * * * *